(12) United States Patent
Qiang et al.

(10) Patent No.: US 6,294,380 B1
(45) Date of Patent: Sep. 25, 2001

(54) LIVER CELL CLONES FOR USE IN EXTRACORPOREAL LIVER-ASSIST DEVICE

(75) Inventors: Shi Qiang, Tianjin (CN); Hajime Kimura, Tokyo-To (JP); Horst Klinkmann, Rostock (DE); Izumi Kazuo, Hiroshima (JP)

(73) Assignee: JMS Co., Ltd. (JP)

( * ) Notice: Subject to any disclaimer, the term of this patent is extended or adjusted under 35 U.S.C. 154(b) by 0 days.

(21) Appl. No.: 09/363,871

(22) Filed: Jul. 29, 1999

(51) Int. Cl.[7] ....................................................... C12N 5/00
(52) U.S. Cl. ........................ 435/325; 424/93.7; 435/1.1; 435/284.1; 435/289.1; 435/370; 435/395
(58) Field of Search .................................... 435/325, 370, 435/395, 284.1, 289.1, 1.1; 424/93.7

(56) References Cited

FOREIGN PATENT DOCUMENTS

WO 96/09876    4/1996   (WO) .

OTHER PUBLICATIONS

Kamlot, et al., Review: Artificial Liver Support Systems, Biotechnology and Bioengineering, 50(4) (May 1996) 382–391.

Sussman, et al., Treatment of Hepatic Failure–1996: Current Concepts and Progress Toward Liver Dialysis, American Journal of Kidney Diseases, 27(5) (May 1996) 605–621.

Sussman, et al., Artificial Liver Support, Clinical and Investigative Medicine, 19(5) (Oct. 1996) 393–399.

Dixit, et al., Artificial Liver Support: State of the Art, Scandinavian Journal of Gastroenterology, (31) (1996) Suppl 220:101–14.

Hughes, et al., Use of Bioartificial and Artificial Live Support Devices, Seminars in Liver Disease, 16(4) (Nov. 1996) 435–444.

Gerlach, et al, Experimental Evaluation of a Hybrid Liver Support System, Transplantation Proceedings, 29 (1997) 852.

Hiroaki, et al., Targeting Vector for Producing Physiologically Active Substance, Patent Abstracts of Japan, Japanese Patent Office, No. 10–94393, Apr. 14, 1998.

Shizushi, et al., Hybrid Type Artificial Liver, Patent Abstracts of Japan, Japanese Patent Office, No. 10–234850, Sep. 8, 1998.

*Primary Examiner*—Leon B. Lankford, Jr.
(74) *Attorney, Agent, or Firm*—Pillsbury Winthrop LLP

(57) ABSTRACT

A blood perfusion device or apparatus that is used for bioartificial liver support. Human hepatocyte lines established from normal regenerating liver tissue and modulated in toxin-challenging conditions are provided. These functional hepatocytes exhibit extraordinarily enhanced detoxification functions, which are characterized by the elevated glutathione content and glutathione S-transferase activity. A bioreactor is constructed with the functional hepatocytes for bioartificial liver support system, which includes perfusion inlets and perfusion outlets, a containment vessel, a centrifugal pump and macroporous microcarriers where the functional hepatocytes are grown.

12 Claims, 2 Drawing Sheets

LIVER CELL CLONES FOR USE IN EXTRACORPOREAL LIVER-ASSIST DEVICE

BACKGROUND OF THE INVENTION

1. Field of Invention

The present invention generally relates to a liver-assist device and liver cell clones which may find application in artificial liver systems, extracorporeal liver-assist devices and bioreactors. More particularly, the present invention is directed to a liver cell clone with enhanced detoxification activities. The liver cell clone is characterized as having increased GSH content and elevated GST activity as compared to conventional immortalized human hepatocyte cell lines and primary human hepatocyte cultures isolated from liver tissue.

2. Background of the Related Art

Over the past several years, the focus of investigations employing extracorporeal liver support systems for the treatment of fulminant liver failure and liver dysfunction has been shifting from basic experimentation and animal trials to clinical evaluations and applications. Some groups in the United States are conducting, under the supervision of the Food and Drug Administration, clinical trials with various bioartificial liver devices (See, e.g., Rozga J. et al., J. Ann. Surg. 219:538–46, 1994, Sussman N. L. et al., Amer. J. Kid. Dis. 18:371–84, 1996, Sussman N. L., Clin Invest. Med. 19:393–9, 1996, Dixit V., Scan. J. Gastroenterol. Suppl. 220:101–14, 1996). Similarly, several groups in Euro-Asia (in particular, Germany, the Netherlands, Great Britain, and Russia) have commenced pre-clinical trials into the effectiveness of bioartificial-liver devices in treating liver dysfunctions (See, e.g., Gerlach J., Transplant. Proc. 29:852, 1997, Hughes R. D et al., Semin. Liver Dis. 16:435–444, 1996). Research into bioartificial liver support devices is also quite active in Japan.

The immediate objective of temporary liver support (which may be provided by bioartifical-liver devices) is to maintain a patient with acute or fulminant hepatic failure or dysfunction until the patient's own liver regenerates. From the clinical data available, it appears that liver support systems are mainly used to bridge the patient to orthotopic transplantation, to improve cerebral circulation and to improve hemo-dynamic parameters.

Rozga and his group have reported on 19 patients treated with bioartificial liver (BAL) devices for 7-hour periods on one to five occasions. Two groups of patients were studied, eleven (11) with acute liver failure and eight (8) with chronic liver failure. Liver transplantation was performed at a mean of 39 hours after initiating BAL support. Thirteen (13) patients, all eleven (11) suffering from acute liver failure and two (2) of the chronic liver failure group, survived after liver transplantation. Patients who were not candidates for transplantation, and therefore did not receive a liver transplant, died (Kamlot A. and Rozga J., Biotech & Bioeng. 50:382–91, 1996).

In a clinical study carried out by Sussman et al. (Sussman N. L. et al., Amer. J. Kid. Dis. 18:371–84, 1996), eleven (11) patients with acute liver failure were treated with an extra-corporeal liver assist device (ELAD) for up to 114 hours. Nine of ten patients in whom multiple estimations of galactose elimination capacity were measured showed improved galactose elimination capacity. One (1) patient recovered without transplantation, four (4) patients underwent transplantation, and the others died.

Only occasionally has treatment with bioartificial liver support systems, ELAD or BAL, alone been shown to lead to complete recovery (Sheil A. G. R. et al., Aust. N. Z. J. Surg. 66:547–52, 1996; Watanabe F. D. et al., Ann. Surg. 225:484–91, 1997). Further, although hepatocyte-based hybrid extracorporeal livier support devices have demonstrated significant improvement in metabolic functions in a variety of experimental and animal tests, such degree of improvement has been difficult to duplicate completely in humans. The efficiency of treatment demonstrated in human patients suffering from hepatic failure is not so striking as compared to the efficiency seen in animals, as shown in those patients who are treated with either of the two most widely used extracorporeal liver-assist systems. For example, a well-controlled clinical trial recently carried out in the U.K to assess the overall value of ELAD (Sussmann) and BAL (Rozga) in the treatment of patients suffering from hepatic dysfunction, showed that while the two systems enhanced certain metabolic functions in such patients, the magnitude of the enhancement was not at a desired level (Hughes R. D. et al., Semin. Liver Dis. 16:435–444, 1996). Similar studies suggest that the functional capacity of conventional extracoporeal liver-assist devices may be limited, particularly considering the number of metabolic functions needing correction in the fulminant patient.

Numerous obstacles have impeded the development of efficient extracorporeal liver-support devices for routine clinical application. These are: (1) an imperfect understanding of the basic pathophysiology of liver dysfunction, liver biology and the regulation of the proliferation of hepatocytes; (2) absence of knowledge in regard to the mechanisms involved in the development of hepatic coma and/or encephalopathy in fulminant hepatic failure; (3) an inability to produce, and maintain in a bioreactor, a sufficient number of hepatocytes with sufficient. bio-activity to correct failing liver functions in fulminant hepatic failure patients. At present, hepatocytes used in conventional extracorporeal liver-assist devices are typically harvested from primary liver cultures obtained from animals, particularly the pig, or consist of immortalized cells derived from humans. Fresh hepatocytes have the advantage of differentiated functionality, but lack proliferation ability. The situation is Just reverse in term of immortalized cells. These two types of hepatocytes are often at opposite ends of a biologic continuum.

As differentiation and proliferation are found to be incompatible in a large number of cell types (evidently in accord with some basic biological principle), it is often difficult to obtain large number of hepatocytes with desired multiple functionalities. Common BAL devices contain about 50 g primary cultures from pig liver, which is significantly lower than that physiologically minimal mass (ranging from 200–400 g) hypothesized to be needed for efficient metabolic activity. On the other hand, even ELAD devices employing as much as 400 g of C3A immortalized cells have provided insufficient major synthetic and metabolic functions (Hughes R D et al, Liver Transpl Surg 1:200–6, 1995). For example, Gailetti et al. conducted a study which ostensibly used adequate amounts of primary hepatocyte cultures in a complex and well-designed configuration, desirable function could only be found for a limited period of about 7 hours (Gailetti P. M. & Jauregui H. O., in Handbook of Bioengineering pp 1952–66, 1995).

At this time, continuous support of patients with fulminant hepatic failure appears to be impractical using fresh pig livers. Further, no method has been developed yet which adequately prevents hepatocytes from a human or porcine source from deteriorating in vitro. Although great efforts have been made to improve the performance of hepatocytes in such systems, including primary culture from xenograft and established cell lines, no report has claimed to maintain desired functions of differentiated hepatocytes for significant periods of time in bioartificial liver-support system bioreactors. Loss of hepatic functions in culture appears to be associated with cellular responses involving cellular interactions and cellular apoptosis in vitro (Collins B. H. et al., Transplantation 58:1162–71, 1994); Rivern D. J. et al. Transplant Proc. 31:671–73, 1999). It should be noted that cells isolated from the body are maintained in a non-physiologic environment and are cut off from numerous regulatory mechanisms which control hepatocyte function in vivo. It appears that the hepatocyte bioreactors for bioartificial liver support have reached their maximal performance at present, and that further improvement will not be seen unless there are theoretical and technological breakthroughs made to harvest multiple functional hepatocytes.

On the whole, it may be argued that bioartificial liver systems fail to show a significant advantage over totally artificial liver systems. Some artificial liver systems, such as those based on modern membrane technology and absorbents, have already been the subject of positive clinical assessment (Ash S. R. et al., Intl. J. Artif. Org. 15:151–61, 1992). For example, highly adsorptive dialysis membrane coated with albumin has been reported to facilitate the removal of toxins (Stange J. et al., Artif. Org. 17:809–13, 1993). As BAL systems conventionally use traditional charcoal adsorbents in the plasma circuit before the hepatocyte bioreactor (Rozga J. & Demetriou A. A., ASAIO J. 41:831–37, 1995), it is difficult to assess how much of the effect seen with BAL treatment is due to the charcoal, and how much due to the hepatocytes in the bioreactor.

It is also important to sort out the priority in which toxins should be removed. In general, both total artificial and bioartificial liver support systems have been designed to remove a dozen or so potential toxins that are recognized as factors causing encephalopathy in hepatic failure patients. Removal of the toxins is generally accomplished by use of adsorbents, dialysis, and viable hepatocytes. Unfortunately in the clinic, however, patient outcome has not always been found to be proportional to the circulating level of any these toxins, such as ammonia, imbalanced amino acids. It remains uncertain whether hepatic coma is due to any one toxin, a synergistic effect between toxins, or other factor.

In hepatic failure, the toxic substances come from two sources. They enter into the systemic circulation because of failure of the liver to clear substances from portal blood. Toxins also accumulate in a patient's circulation as result of necrosis of the liver tissue itself. Less is known about the nature and role of the necrotic substances in the development of encephalopathy than with respect to the toxins that are not cleared by the dysfunctional liver. There is, however, some indirect evidence implicating the importance of these necrotic substances. For example, it is known that when necrotic tissue is removed from patient body, i.e, hepatectomy is carried out before transplantation, improvement in systemic hemodynamic parameters (systemic vascular resistance and oxygen utilization) and reduction in intracranial pressure (ICP) can be achieved (Ringe B. et al., Transplant Proc. 20:552–7, 1988; Harrison P M et al., Gut 32:A837, 1991). Patients receiving orthotopic liver transplantation after treatment with extracorporeal liver support fare significantly better than patients not receiving transplantation, presumably because the necrotic liver in such patients is not removed.

Necrotic tissue can release some toxic metabolites that include a considerable amount of reactive oxygen substance species. Oxidative stress results in mitochondrial dysfunction, membrane injury and denaturation of DNA and other cell components (Sewell R. B. et al., Clin. Sci. 63:237, 1982). Excessive production of oxygen radicals may lead to altered enzymatic activities, decreased DNA repair, impaired utilization of oxygen, glutathione depletion and lipid peroxidation. The circulating toxins can cause pathological changes such as inflammatory reactions in all part of body, but in particular cerebral cells that are quite sensitive to these toxins. Damage to the cerebral cells may result in cerebral edema featured by increased intracranial pressure. Failure to obtain proper treatment may lead to other complications such as multiple organ failure (MOF), onset of severe clotting abnormalities, renal failure, pulmonary edema or cardiovascular collapse. It has been hypothesized that encepchalopathy is an early symptom of multiple organ failure caused by toxins released from necrotic liver tissue. There are also a few reports that indicate the involvement of active oxygen species toxins from necrotic tissue in the development of hepatic coma. As eradication of necrotic toxins might be an alternative to bioartificial liver support, such eradication may play an increasing role in the future design of bioreactors for liver support systems.

It has been suggested that an extracorporeal artificial liver support system does not necessarily require that hepatocytes used be able to replace all missing bio-functionality, and that some specific functional activities that happen to be missing or deficient in the patients might be ameliorated in an alternative manner.

Acute liver failure is usually associated with hepatic encephalopathy, which results in high mortality. The main purpose of an artificial liver-support system is to prevent the patient suffering from fulminant hepatic failure from developing encephalopathy, or to treat encephalopathy if it has already developed. The reversible and global nature of hepatic encephalopathy strongly indicates that a metabolic abnormality rather than direct toxic injury is involved in its pathogenesis. There is also a great deal of evidence to demonstrate that many toxins accumulate in a patient's circulation upon hepatic failure, and that such toxins may be responsible for the initiation of encephalopathy. Therefore, detoxification or removal of toxins from patients suffering from fulminant hepatic failure is considered to be a primary goal of extracorporeal liver-assist devices. Previous studies on the removal of toxins from the blood of patients using absorbents or dialysis have not demonstrated significant improvement in the survival of patient's suffering from severe encephalopathy. The present inventors hypothesize that blood purification needs to become more specific and selective in order to provide a useful remedy for reducing the severity of hepatic encephalopathy.

SUMMARY OF THE INVENTION

The present invention generally relates a liver-assist device and to liver cell clones which may find application in artificial liver systems. extracorporeal liver-assist devices and bioreactors.

An embodiment of the present invention is directed to a specific extracorporeal liver assist device (sELAD) which incorporates a novel human hepatocyte cell line and macroporous microcarrier culture. The human hepatocyte cell line (DYD) is derived from human regenerating liver tissue and is modified to have enhanced specific detoxification functions in vitro. The liver cell clone is characterized as having increased GSH content and elevated GST activity, as compared to its parental cell, while expressing many of the characteristics of a normal human hepatocyte liver cell clone. DYD hepatocytes are useful in detoxifying toxins from necrotic liver tissue (which is considered to be one of the most important factors in the development of hepatic encephalopathy in fulminate hepatic failure). Such hepatocytes are advantageously grown on macroporous microcarriers, preferably resulting in a 2.5–7.5×10$^{10}$ accommodation per bioreactor module. Improvement both in quality and quantity of inoculated cells in the bioreactor makes SELAD an attractive therapeutic remedy to treat the patient with fulminate hepatic failure.

DETAILED DESCRIPTION OF THE INVENTION AND PREFERRED EMBODIMENTS

Figure 1:
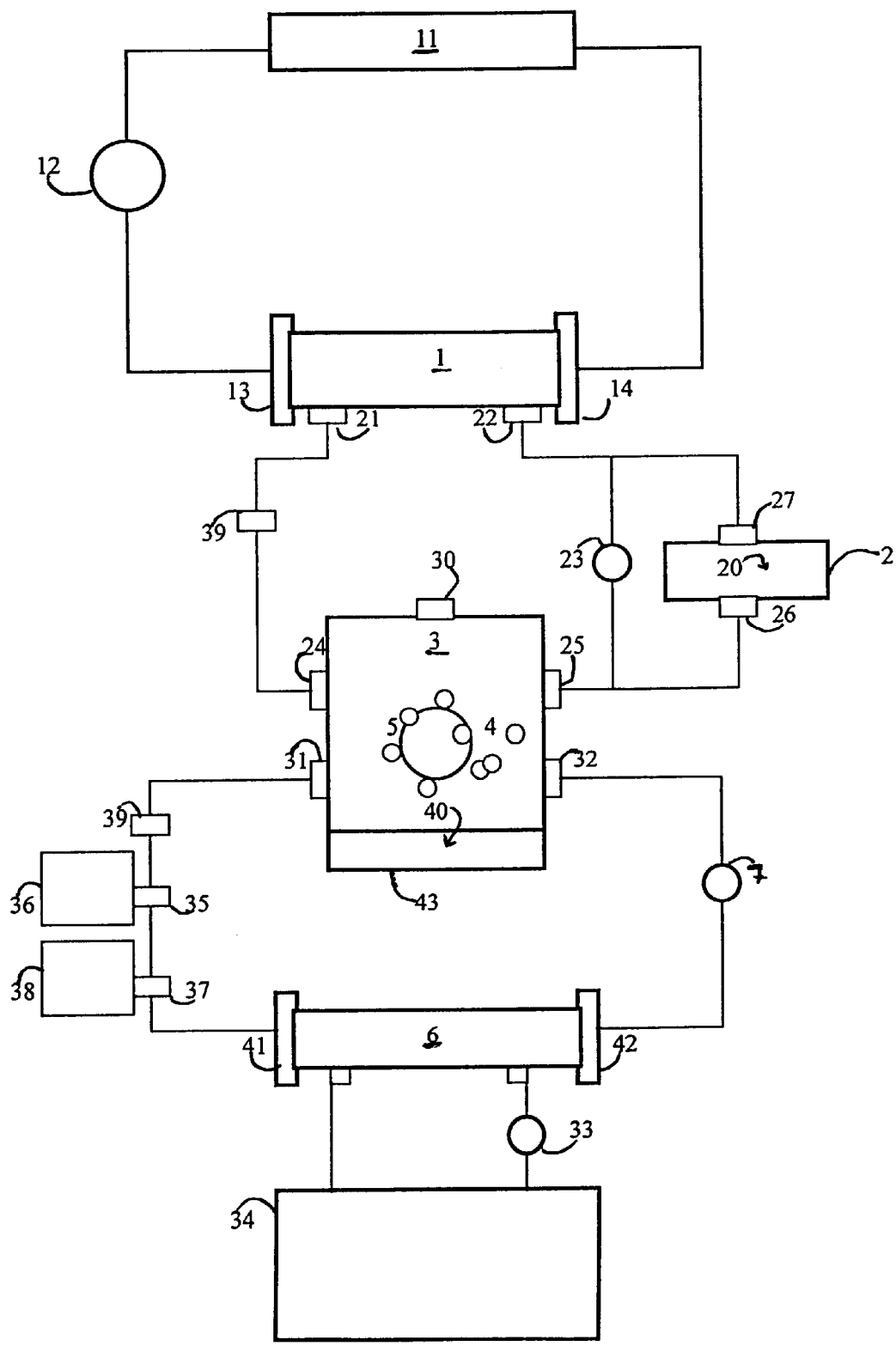
FIG. 1 is a cross-sectional diagrammatic view of an extracorporeal liver-assist device (sELAD) of the present invention that preferentially uses special functional hepatocytes with enhanced detoxification functions.

The present invention relates to a liver-assist device and to liver cell clones, which may find application in such device.

An embodiment of the present invention is a novel detoxification system, referred to as a "specific Extracorporeal Liver Assist Device" ("sELAD"), which is based on a special functional hepatocyte cell line. By the term "specific Extracorporeal Liver Assist Device" it is meant an extracorporeal liver support system which provides augmentation of functional activities which are typically diminished in hepatic dysfunction, and which are considered important in the recovery from hepatic coma, frequently seen in fulminant hepatic failure patients. Since it is difficult to obtain an extracorporeal liver support system which displays all of the biochemical potential of hepatocytes in vivo, the system may possesses some of the main hepatic functions, preferentially detoxification. Preferably the extracorporeal liver support system possesses enhanced or elevated detoxification function by way of employment of hepatocytes, inoculated into the system, which have several times higher the content of detoxification enzymes and detoxificants than freshly isolated or transformed hepatocytes.

A bioartificial liver support system that applies the principles of the present invention provides an effective alternative to treat patients with fulminant hepatic failure. The device and method of the present invention can be used not only in bridging the patient to orthotopic transplantation, but also in preventing the patient from developing encephalopathy.

The immediate objective of any extracorporeal liver-support system is to maintain a patient with fulminant hepatic failure until the patient's own liver regenerates, or to bridge the patient to orthotropic transplantation. Most liver support systems used today are directed to blood detoxification because detoxification is considered an essential requirement for an extracorporeal liver support system. The metabolism of toxic substances by living cells in a hepatocyte bioreactor reduces toxicity, thus producing beneficial effects for the recovery of patients.

One embodiment of the present invention describes a method and apparatus to enhance detoxification activity in immortalized human hepatocytes by a cellular approach. The pathway to enhance the specific detoxification functions of the hepatocyte, which is described in this invention, is to modulate glutathione (GSH) and glutathione S-transferase (GST) levels in an immortalized human hepatocyte line (DYD). Using the present disclosure, one may produce such cells in a sufficient mass equivalent to the counterpart in vivo.

The glutathione and glutathione S-transferase system (GSH/GST) play an important role in removing toxic substances accumulating in the circulation of liver failure patients. GSH is a prevalent low molecular weight peptide that has multiple physiological and metabolic functions. GSH participates in reactions that destroy hydrogen peroxide, organic peroxides, free radicals and foreign compounds and drugs. GSH also participates in the metabolism of various endogenous compounds. Evidence suggests that GST is involved in protection against oxidative stresses (Lenehan P. F. et al., Cancer Chemother. Pharmacol. 35:377–86, 1995). The GSH/GST pathway represents part of an adaptive response mechanism to chemical stress caused by electrophiles, activated forms of most metabolites.

Eukaryotic cells have evolved several mechanisms to protect cellular constituents from highly reactive molecules entering or being biotransformed in the cells. The greater affinity of electrophiles for thiol groups, than for hydroxyl or amine groups, provides a chemical-physical basis for using high concentrations of substances containing thiol moieties as protectants. The formation of .a thioether bond between electrophiles and GSH typically yields a conjugate that is less reactive than the parental compound, therefore, the actions of GSH generally result in detoxification. GSH conjugation with harmful electrophilic moieties increases the solubility of hydrophobic xenobiotics, which then can more easily be transported out of the cells by the ATP-dependent glutathione S-conjugate efflux pump (GSH-Px).

It has been reported that induction of the GSH/GST pathway detoxifies some of the toxic carbonyl-, peroxide-, epoxide-containing metabolites produced within the cell by oxidative stress (Meister A. in The liver: Biology and Pathology, 1988 by Raven Press, Ltd., New York). As GSH functions in protecting cells from reactive oxygen intermediates, free radicals and toxic compounds, an increase in cellular GSH levels, and GST activity, may be beneficial. For example, some clinical studies have shown that liver damage can be prevented and minimized by the application of a glutathione precursor (Prescott L. F. et al., Lancet 2:10913, 1976; Rumack B H et al., Arch. Intern. Med. 141:3 80–5, 1981; Smilkstein M. J. et al., N. Eng. J. Med. 319:1557–62, 1988).

Cellular GSH levels may be partially increased by supplying substrates for enzymes in GSH synthesis. The constitutive upregulation of GSH synthesis and GST activity can also be achieved by modulating the cells under a progressively toxin-challenging culture (Hamilton T. C., in Glutathione S-Transferase Structure, Function and Clinical Implications, pp. 173–85, 1996) (so does the induction of cellular defense system to the oxidants).

GST activity is increased in many organisms following exposure to select foreign compounds. Induction of GST has been most thoroughly studied in rodents, and at least 100 different chemicals have been discerned to induce GST in rats and mice. The wide spectrum of xenobiotics that act as GST inducing agents, suggest that GST induction is part of an adaptive response mechanism to chemical stress that is widely distributed in nature. From studies of rodents, it may be inferred that the adaptive response to chemical stress is clearly pleiotropic in character and involves the induction of many drug metabolizing enzymes. Collectively, these detoxification enzymes provide protection against a diverse spectrum of harmful compounds.

The conjugation reaction between GSH and xenobiotics represents the first step in the synthesis of mercapturic acids, an important group of excretion products. Following conjugation with GSH, the subsequent steps in mercapturic acid biosynthesis require the serial actions of glutamyl transpeptidie, cysteinyl glycinase, and N-acetyl transferase. Since GSH functions in protecting cells from reactive oxygen intermediates, free radicals and toxic compounds, an increase in cellular GSH level and GST activity may be beneficial under certain clinical conditions, such as hepatic coma in which a significant amount of toxins from necrotic tissue flushes into the blood stream.

It is preferred in the present invention that modulation of intracellular GSH content and GST activity be carried out in an immortalized hepatic cell line. A preferred cell line is designated DYD, a human hepatocyte clone established from normal liver tissue. DYD is a highly differentiated cell line capable of growing at a high density. By endowing such cells with specific detoxification functions, the cells have the ability to transform toxins more specifically, rapidly and efficiently, thus elevating the efficiency of a bioreactor in a bioartificial liver-support system.

The quantity of hepatocytes inoculated into a bioreactor is another important factor that influences the efficiency of current bioartificial liver support systems. Although the exact number of hepatocytes in a convention bioreactor is not known, it is generally accepted that the cell mass is in the order of 100–300 g extracorporeal support.

The number of cells in a single bioreactor of the present invention is is preferably about 2.5–7.5 billion in magnitude, about 25–75 gram per single module. In order to accommodate such a huge number of cells, a special bioreactor configuration was designed. The cells were allowed to grow to confluence on inacroporous microcarriers. The cell-attached microcarriers where then moved into a bioreactor, where a continuous supply of nutrition and oxygen was provided to guarantee maintenance of steady functioning of the hepatocytes.

In modulation of the detoxification function, it was determined that highly differentiated human hepatocytes are optimal. An immortalized cell line with highly differentiated functions is preferred. Besides providing an unlimited cell division capacity, immortalized human hepatocytes obviate concerns about species specific metabolic differences. Further any infusion of proteins from the human hepatocytes is less likely to cause immune-mediated reactions than non-human proteins, especially after prolonged or repeated use. Methods for the establishment of immortalized cell lines are well known in the art, and are available using advanced cell and tissue culture technology. However, in order to obtain a clonal expansion of hepatocytes from normal liver tissue, special procedures in developing cell line are necessary, such as the use of new type matrix, growth factors or conditioned medium and induction of clonal expansion.

Enhancement of differentiated he patocyte functions, specifically those functions specific to detoxification, can be brought about by the induction and regulation of glutathione S-transferase, which is considered, as stated above, to represent a major group of detoxification enzymes. All eukaryotic species possess multiple cytosolic and membrane-bound GST isoenzymes, each of which displays distinct catalytic as well as non-catalytic binding properties (Hayes J. D. et al., Crit. Rev Biochem. Mol. Biol. 30:445–600, 1995). Through the concerted actions of several isoenzymes, the GST supergene family provides several tiers of defense against toxic chemicals. Evidence suggests that the level of expression of GST is a crucial factor in determining the sensitivity of cells to a broad spectrum of toxic chemicals.

It is known that some enhancers can regulate GST expression in the animal cells. Some enhancers interact with GST gene elements that respond to xenobiotics. They transcriptionally activate GST genes through different mechanisms according to their elemental structure (Hayes J. D. et al., Critical Reviews in Biochemistry and Molecular Biology 30: 445–600, 1995). The constitutive expression of GST up-regulation can be achieved by the effective modulations.

The constitutive up-regulation of GSH synthesis and GST activity can be achieved by modulating the cells under a toxin challenging culture condition. The chemicals that induce GST and GSH are extremely diverse. These include carcinogens, cytotoxins, chemotherapeutic drugs, heavy metals and metal-containing drugs. GST induction can also be performed using reactive oxygen species. Examples of chemicals inducing GST and GSH include: N-acetoxy-2-amino-1-methyl-6-phenylimidazo[4, 5-b]pyridine, aflatoxin $B_1$-8,9-epoxide, benzo[a]pyrene-4,5-oxide, benz[a]anthracene-5,6-oxide, benz[a]anthracene-8,9-diol-10,11-oxide, butadiene monoepoxide, +anti chrysene-1,2-diol-3,4-oxide, 5-hydroxymethylchrysene sulfate, 7,12-dihydroxymethyl-benzo[a]anthracene sulfate, 7-hydroxymethyl-12methylbenz[a]anthracene sulfate, 1-methyl-2-nitro-1-nitrosoguanidine, 1-nitropyrene-4,5-oxide, 1-nitropyrene-9,10-oxide, 4-nitroquinoline 1-oxide, benzo[a]pyrene, dimethylaminoazobenzene, 7,12-dimethylbenz[a]anthracene, 5,9-dimethyl-7H-dibenzo[c,g] carbazole, 3-methylcholanthrene, acetochlor, acifluorfen, alachlor, aldrin, atrazine, azinphosmethyl, 1,4-benzoquinone, chlorimuron ethyl, cumen hydroperoxide, DDT, N,N-diallyl-2-chloroacetamide, diazinon, dichlobenil, dichlofluanid, 2,4-dichlorophenoxyacetic acid, S-ethyl N,N-dipropylthiocarbamate sulfoxide, ethylene oxide, ethylparathion, fenoxapropethyl, fluorodifen, lindane, malathion, methyl bromide, methyl chloride, methyl parathion, metolachlor, trans, trans-muconaldehyde, naphthalene 1,2-oxide, parathion, propachlor, propetamphos, styrene oxide, tetrachlorvinphos, trans-stilbene oxide, tridiphane, vinyl chloride, ampicillin, fosfomycin, penicillin, 1,3-bis(2-chloroethyl)-1-nitrosourea, chlorambucil, cyclophosphamide, ethacrynic acid, mechlorethamine, melphalan, mitozantrone, nitrogen mustard, thiotepa, acrolein, adenine propenal, cholesterol α-oxide, cytosine propenal, dilinoleoylphosphatidylcholine hydroperoxide, dilinoleoylphosphatidylethanolamine hydroperoxide, dilinoleoylphosphatidylglycerol hydroperoxide, epoxyeicosatrienoic acid, 4-hydroxynonenal, linoleic acid hydroperoxide, methyl linoleate ozonide, thymine propenal, uracil propenal, chlorotrifluoroethane, 1,4-dibromo-2,3-epoxybutane, dibromomethane, 1,3-dichloroacetone, dichloroacetylene, dichloromethane, 1,2,3,4-diepoxybutane, 1,2-epoxy-4-bromobutane, ethylenedibromide, hexachlorobutadiene, allobarbital, 1-β-D-arabinofuranosyl cytosine, barbital, bisethylxanthogen, butylated hydroxyanisole, butylated hydroxytoluene, 3,5-di-tert-butylcatechol, tert-butylhydroquinone, 2-n-butylthiophene, cisplatin, clonazepam, cyclophosphamide, dexamethasone, diethyldithiocarbamate, diethyl maleate, diethylnitrosamine, 5,6-dihydro-2H-pyran-2one, dimethyl fitmarate, dimethyl maleate, dimethyl itaconate, disulfiram, 1,2-dithiole-3-thione, erucin, erysolin, ethanol, ethoxyquin, 5-ethyl-5-phenylhydantoin, 2-n-heptylftiran, α-hexachlorocyclohexane, γ-hexachlorocyclohexane, hexachlorobenzene, 3,4,5,3',4',5'-hexachlorobiphenyl, 2,4,5,2',4',5'-hexachlorobiphenyl, 2,3,5,2',3',5'-hexachlorobiphenyl, interferon-α/β, iproplatin, isosafrole, lead acetate, p-methoxyphenol, methyl acrylate, 3-methylcholanthrene, 2-methylene-4-butyrolactcne, methyl selenocyanate, musk xylene, β-naphthoflavone, oltipraz, phenobarbital, polychlorinated biphenyl, propylthiouracil, rifampicin, trans-stilbene oxide, steptozotocin, sudan, 1,4-bis-[2-(3,5-dichloropyridyloxy)]benzene, tetrachlorodibenzo-p-dioxine, 2,3,5,6-tetrafluorophenol, 1-(2-thiazolylazo)-2-naphthol, vinylidene chloride, adriamycin, arsenic, bleomycin, 2-[3-(chloroethyl)-3-nitrosoureido]-D-dioxyglucopyiranose, ethacrynic acid, etoposide, hepsulfam, mitomycin C, mitoxantrone, novantione, oxazaphosphorine, TGF-β1 and vincristine. It appears that the majority of GST substrates are either xenobiotics or products of oxidative stress in nature. The common feature for these compounds is that they are involved in the metabolizing process or the generation of metabolic cascade. Some endogenous compounds are also inducers of GST.

Modulation of intracellular GSH content and GST activity may be carried out in a replicating hepatic cell line DYD, a human hepatocyte clone established from normal liver tissue. A modulating procedure such as described in Example 1 below may be undertaken. By endowing the DYD hepatic cells with enhanced specific detoxification functions, the hepatocytes can transform toxins more specifically, rapidly and efficiently, thus elevating the efficiency of bioreactor for bioartificial liver support system.

An embodiment of the present invention comprises functional human liver cell clones (DYD-) derived from a normal human hepatocyte cell line (DYD) which exhibits enhanced detoxification activities as characterized by increased GSH content and elevated GST activity. The functional human liver cell clones preferably elicit increased GSH content and elevated GST activity as compared to immortalized human hepatocytes cell lines and a primary human hepatocyte culture isolated from human liver tissue. A particularly advantageous cell line, demonstrating unexpectedly superior properties, has a GSH content above 50 nmol/mg protein or 50 nmol/$10^6$ cells; after 24 hours passage and a GST activity above 15 nmol/mg protein/min or 80 nmol/$10^6$ cells /min with CDNB as substrate after 24 hours passage.

In another embodiment of the present invention, there is disclosed a method to obtain the functional human liver cell clones eliciting increased GSH content and elevated GST activity as compared to immortalized human hepatocytes cell lines and a primary human hepatocyte culture isolated from human liver tissue, which comprises a process of exposing a normal hepatocyte cell line in culture medium to to a toxin and modulating the expression of GSH and GST with inducers. The inducers may possess a carcinogenic or cytotoxic nature.

In another embodiment of the present invention, there is disclosed an extracorporeal liver-assist device, which has a bioreactor containing functional human liver cell clones eliciting increased GSH content and elevated GST activity as compared to immortalized human hepatocytes cell lines and a primary human hepatocyte culture isolated from human liver tissue. Preferably, the functional human liver cell clones are grown on macroporous microcarriers or other biocompatible support matrix system, for example, capillaries or ceramics. Preferably, the extracorporeal liver-assist device comprises plasma filtration circulation system and dialysis cirtridge circulation system. The plasma filtration circulation system may employ an adsorbent column.

In yet a further embodiment of the present invention, there is disclosed a method to obtain the functional human liver cell clones eliciting increased GSH content and elevated GST activity as compared to immortalized human hepatocytes cell lines and a primary human hepatocyte culture isolated from human liver tissue, which comprises a process of exposing a normal hepatocyte cell line in culture medium over a period of time to increasing concentrations of a compound that induces GSH and GST. The inducer compounds may possess a carcinogenic or cytotoxic nature.

EXAMPLE 1

Establishment of a Functional Human Hepatocyte Cell Line and its Modulation of GSH Content and GST Activity All cell culture reagents, including William's E medium, fetal calf serum (FCS), penicillin-streptomycin, sodium pyruvate and L-glutamine, were purchased from Gibco Life Technologies Ltd. All other chemicals were purchased from Sigma (St, Louis, USA) unless otherwise mentioned. The established human liver DYD cells were grown as a monolayer culture in William's E supplemented with 10% (v/v) FCS in an atmosphere of 5% $CO_2$ in air. Cells were subcultured once a week at a split ratio of 1:3 using trypsin and EDTA. Cisplatin was purchased from Sigma, St. Louis, USA. It was dissolved in Hans' solution. Stock solution was kept in −20° C. The stock solution was diluted according to the concentrations needed for the culture medium. Cisplatin (cis-diaminedichloroplatinum; cis-DDP) is a chemotherapeutic drug used to treat a wide spectrum of tumors. The mechanism of cisplatiin is to kill the cells by causing cytotoxicity. The GSH content and GST activity of the established human liver cell line DYD was modified using cisplatin in order to obtain specially functional hepatocytes characterized by having a higher capacity for detoxification functions than its parental cell.

Medium without cisplatin was used as routinely to culture the DYD cells. DYD cells were treated with 0.5 µg/ml cisplatin for 24 hours in the medium, which was supplemented with serum weekly. This procedure was repeated using increasing concentrations of cisplatin, from 0.5 µmg/ml to 5.0 µg/ml, over a ten-month treatment. The cells were cloned, and the cloned cells stored in liquid nitrogen. Each set of clones was designated with an initial DYD- descriptor, followed by the lime of cisplatin exposure in weeks.

For GSH and GST determination, DYD cells and their clones were grown in 24 well plates [Costar, USA]. Glutathione and glutathione S-transferase were determined in every batch of cloned cells. Total intracellular glutathione determination was measured fluorimetrically. GST activity in cell homogenates was determined by direct spectrophotometry using 50 µM 1-chloro-2,4-dinitrobenezene (CDNB).

Table I gives the GSH contents and GST activities in three different clones of DYD cells. GSH contents in these three clones were compared with that of the parental cells from which each was derived as shown in Table 1. GSH levels were elevated in all three clones and correlated with the duration of drug exposure. GST activities were enhanced at different levels in each of the clones. It was hypothesized that in combination with GSH, the increased GST activities might perform an important part in conjugation of toxins to GSH.

TABLE 1

GSH contents and GST activities in parental and modulated cells

|  | Control | DYC-10 | DYD-30 | DYD-50 |
|---|---|---|---|---|
| Toxin exposure time | 0 | 10 weeks | 30 weeks | 50 weeks |
| GSH Content (nmol/mg protein) | 20–40 | 100–150 | 300–400 | 300–500 |
| GST Activity (nmol/mg pro./min) | 5–15 | 15–20 | 20–30 | 20–35 |

EXAMPLE 2

Characterization of the Established Functional Cell Line and its Comparison with Human Primary Culture of Hepatocytes and Immortalized Cells A primary culture of hepatocytes was isolated. from fresh liver tissue. Hepatocytes were digested with 0.25% collagenase, and the cells were dispersed into a balanced salt solution. After washing and filtering through a cell mesh, the cells were seeded in Petri dishes at a concentration of $5 \times 10^6$ in 10 cm dish. DMEM medium was used to culture the cells with 10% FCS. Such cells were compared with Hep G2 cells (an immortalized human cell line) and DYD-50 cells (cells as described in Example 1 having, enhanced GSH content and GST activity).

Table 2 indicates the GSH content and GST activity in the DYD-50 cell line, the immortalized human liver cell line Hep G2 and the primary culture of hepatocytes:

TABLE 2

GSH contents and GST activities in established and primary hepatocytes

|  | Hep G2 cells* | Primary Culture** | DYD-50 |
|---|---|---|---|
| GSH Content (nmol/mg protein) | 10–40 (24 hours subculture) | 20–25 (24 hours culture) | 100–500 (24 hours subculture) |
| GST Activity (nmol/mg pro./min) | 5–15 (24 hours subculture) | 15–20 (24 hours culture) | 20–35 (24 hours subculture) |

*Grant, M. H. et al., Biochemical Pharmacology, 37 (17): 3365–68 (1988)
Doostar, H. et al., Xenobiotica, 20 (4): 435–41 (1990)
**Grant M. H., et al., Biochemical Pharmacology, 36 (14): 2311–16 (1987)

EXAMPLE 3

Scale-up of Established Functional Cells on Macroporous Microcarriers

Macroporous microcarriers were purchased from Pharmacia under the trade names Cytopore™ and Cytoline™ (Cytopore™ is manufactured from cellulose and Cytoline™, a material comprising polyethylene and silica). Before use of the microcarriers, the microcarriers were hydrated and swelled in fresh distilled water or PBS. The distilled water was subsequently replaced with culture medium to equilibrate the microcarriers overnight under culture conditions. In order to provide a homogenous culture environment and to encounter less shearing forces, a perfusion culture system was used to support a high-density cell culture. Fluidized or packed bed reactors were seen as optimal reactors for Cytoline™ microcarriers, in that these reactors combine tile high-density culture of the perfusion technique with low shear forces.

Cell suspensions were prepared by trypsin digestion of cells grown in flasks while the cells were in an exponential growth phase and in good nutritional state. The microcarriers were added to the flasks at a ratio $2 \times 10^6$/ml microcarrier-packed-volume. The flasks were placed into the incubator during the attachment phase, and shaken gently every 30 minutes to obtain uniform cell distributions on the microcarriers. After 5 hours of incubation, sufficient culture medium was added and the microcarriers placed in the bioreactor. It was determined, that in the fluidized bed culture, the maximum volume of packed microcarriers that could be used was 50% of reactor volume. In regard to the packed bed culture, the maximum volume of packed microcarriers that could be used was determined to be 75% of the reactor volume.

In order to obtain high cell density in the bioreactor, toxic metabolites were not allowed to accumulate and pH values were maintained at a set level. The desired level of oxygen concentration was also maintained. Perfused medium was changed periodically. It was found that it typically took 1–2 weeks for DYD hepatocytes to become confluent under the perfusion culture conditions. Upon the harvest of cells, the density could reach $10^7$–$10^8$/ml in a fluidized bed bioreactor.

DESCRIPTION OF THE EMBODIMENTS DISCLOSED IN THE FIGURES

With reference to the embodiment depicted in FIG. 1, there is shown a diagram sketch of a system for bioartificial liver support system made in accordance with the teachings of the present invention. Such support system comprises a plasma separation cartridge for patient circulation 1, an adsorbent column 2, a hepatocyte bioreactor 3, and a dialysis cartridge for nutrient/waste circulation and exchange 6. The hepatocyte bioreactor includes a containment vessel 43, having functional hepatocytes 4 that are grown on macroporous microcarriers 5 at a very high density.

Figure 2:
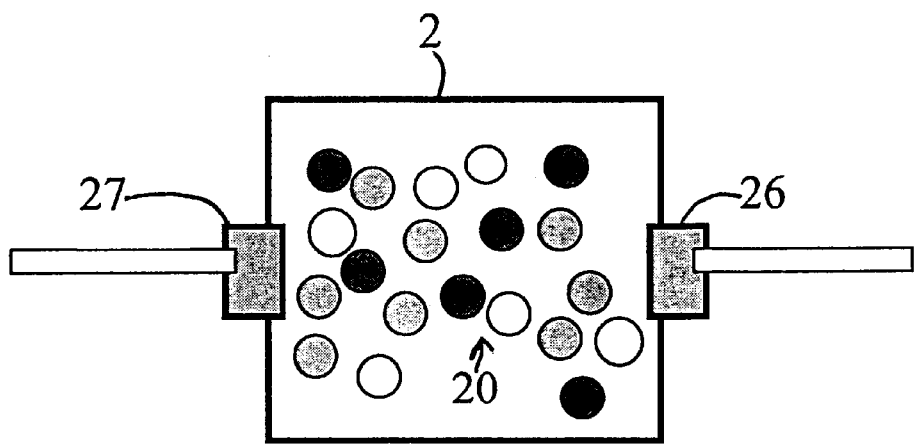
FIG. 2 is a cross-sectional diagrammatic view of an adsorbent column finding use in the present invention.

In the bioartificial liver support system of FIG. 1, blood/plasma from a patient flows through plasma separation cartridge 1 intra-capillarily, while dialysate circulates through bioreactor 3 extra-capillarily at a definite s;peed. The dialysate brings the toxins or substances from a patient into bioreactor 3, where functional hepatocytes 4 are grown on macroporous microcarriers 5. The functional hepatocytes 4 grown on macroporous microcarriers 5 will bio-transform, or metabolize, these toxins or substances into less harmful or non-detrimental metabolites. In order to maintain hepatocyte viability and functionality in culture, a nutrient supply and metabolite removal system is connected with hepatocyte bioreactor 3 by way of dialysis cartridge 6 that is operatively connected between bioreactor 3 and medium reservoir 34. An adsorbent column 2 containing adsorbent 20, and having dialysate inlet 26 and clialysate outlet 27 (more specifically shown in FIG. 2), as well as bioreactor 3, is also operatively connected to patient circulation 11. The patient's circulation 11 is directed by acLion of pump 12 to blood inlet 13 of plasma separation cartridge 1. Activated charcoal is a preferred sorbent. Certain immunological adsorbents, and other known absorbents/adsorbents, can also be used.

Plasma filtration cartridge 1 is shown having inlets 13 and 22 and outlets 14 and 21. A preferred membrane of the cartridge is one which allows efficient exchange of a wide spectrum molecular weight compounds, such as nutrients and toxins accumulating in patients with fulminant hepatic failure, to cross between blood/plasma circulation and hepatocyte bioreactor 3. The chosen membrane of plasma filtration cartridge 1 must be permeable to toxins potentially leading to the development of encephalopathy in fulminant hepatic patients, such as ammonia, aromatic amino acids, fatty acids, mercaptans, endogenous benzodiazepines, bile acids, bilirubin, middle molecules, cytokines, endotoxins and others. As many known toxins are combined with albumin in the patient blood (the albumin acting as a carrier), it is preferred that the desired upper molecular weight limit of the membrane allow the free passage of albumin in order to purify the blood efficiently. A suitable plasma filtration membrane designed for such a purpose is shown installed in this system. Such membranes may be purchased commercially. One preferred type of membrane is made of cellulose, cellulose acetate, polyacryronitrile or polysulphone.

The hepatocyte bioreactor 3 includes a containment vessel 43, wherein the hepatocytes are grown on macroporous microcartiers 5 in a high density, and a centrifugal pump 40. The vessel is constructed with a plastic material that is non-toxic to the cells and has a high mechanical strength. The centrifugal pump 40 is fused at the bottom of the containment vessel 43. There is an opening 30 on the top of containment vessel 43 for hepatocyte injection, and four openings on the two sides of containment vessel 43 designated as dialysate inlets 24, 31 and dialysate outlets 25, 32. The opening on the top 30 is used as injection port of macroporous microcarriers into containment vessel 43. At the mouth of each inlet and outlet, a filter is fixed to avoid cellular entrance into dialysate circulation. Meanwhile, a pressure sensor 39 in the dialysate circulation circuit monitors pressure change indicating circuit clotting.

The dialysate circulation typically comprises culture medium, for example, William's E supplemented with 10–30% normal human serum or plasma. Supplementation with normal human serum or plasma provides for compensation of the failing hepatic synthesis function by infusing human native blood components, increases colloid osmosis in the dialysate, and facilitates mass exchanoe between the patient circulation and dialysate circulation.

To the bottom of containment vessel 43 is fixed a centrifugal pump 40 that keeps the macroporous microcarriers in suspension. Macroporous microcarriers serve as a matrix for anchoring of hepatocytes. In a preferred embodiment, containment vessel 43 is made from polypropylene polycarbonate or polysulfone. A suitable macroporous microcarrier is supplied by Pharmacia LKB Biolechnology under the trade names Cytodex™, Cytopore™ and Cytoline™. The diameter of the macroporous microcarrier is preferably 30–500 $\mu$m, and more preferably 100–300 $\mu$m. The microcarrier is preferably made of cellulose, cross-linked dextran, polyethylene and/or silica.

The viability and functionality of hepatocytes in the bioreactor are maintained by a nutrition supply and metabolite waste removal system. The system illustrated includes a dialysis cartridge 6, having dialysis circulation outlet 41 and dialysis circulation inlet 42, for mass exchange between the hepatocyte bioreactor 3 and the medium reservoir 34. The system further includes a pH sensor 35, a dissolved oxygen sensor 37, and a number of pumps 7, 33. A syringe port 36 to inject pH adjusting solution, and an oxygenator system 38, used to adjust the pH value and dissolved oxygen concentration in intra-capillary circulating fluid, respectively, are also included. Dialysate flows through the extracapillary of dialysis cartridge 6. Dialysate in this part of the system is typically cell culture medium (William's E) without any plasma protein supplements.

The culturing of hepatocytes on the macroporous microcarriers makes it possible to provide, in a practical manner, a high yield culture of anchorage-dependent cells. When using the macroporous microcarriers, the hepatocytes grow not only as monolayer on the surface of microcarrier but also on the inner pores of the microcarrier. Utilization of microcarriers in a suspension or perfusion culture system permits yields of ~$10^7$ up to $10^8$ cells/ml.

Figure 3:
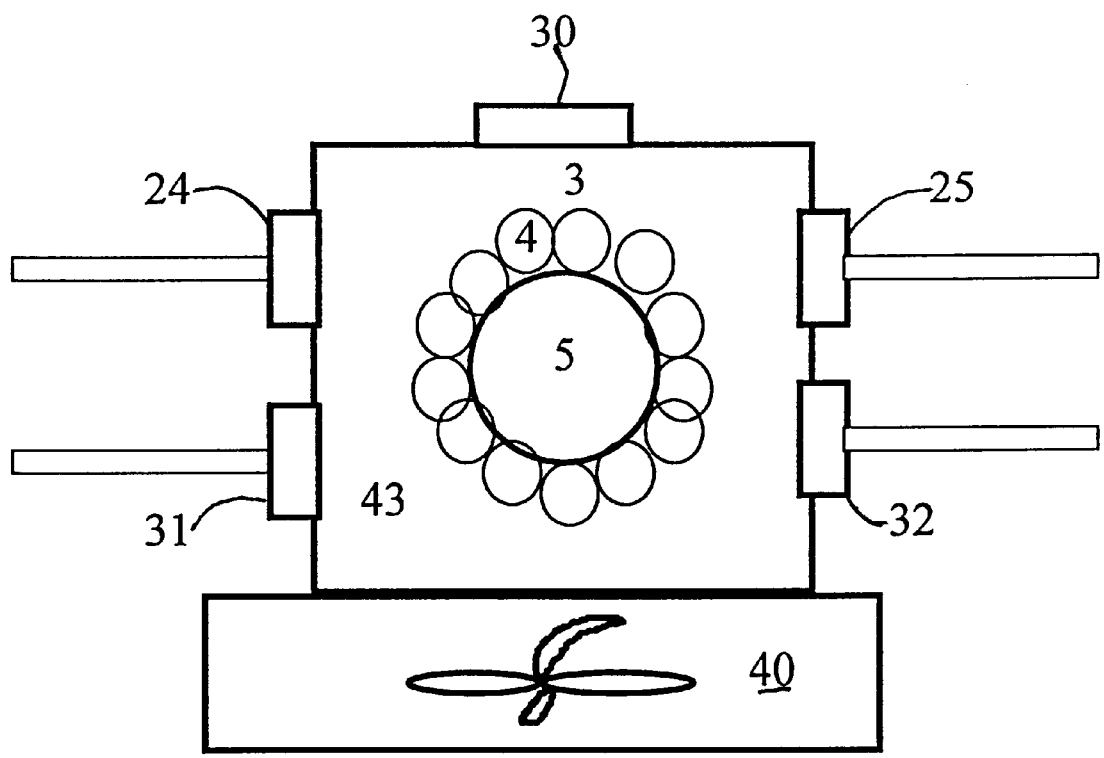
FIG. 3 is a cross-sectional diagrammatic view of a hepatocyte bioreactor finding use in the present invention.

The hepatocyte bioreactor, shown in more detail in FIG. 3, is a central part of the bioartifical liver support system of FIG. 1. Hepatocytes 4 are enclosed in containment vessel 43, about macroporous microcarriers 5 and suspended by action of centrifugal pump 40. It is preferred that containment vessel 43 be fabricated from polypropylene polycarbonate, polystyrene or polysulfone. Such materials proffer several advantages:

1. They have been shown to be non-toxic to cell viability and metabolism.
2. Such materials can be easily sterilized.
3. Such materials may be fabricated in such a manner that the mechanical strength of the containment vessel can easily handle the vibration of centrifugal pump 40 when it is operating.

At the two sides of containment vessel 43 are dialysate inlets 24, 26 and outlets 25, 27. Preferably they are specially manufactured to match the standard plastic fittings for routine dialysis products. Besides di.alysate inlet, and outlets, a filter (not shown in the figure) is mounted at the each mouth of the inlets and outlets so that the cells, and their pieces, or even larger particles are prevented from entering. The pore size of the filter is preferably below 10 um, more preferably between 1–5 um, for successfully preventing leakage of cellular component into, and minimal interference with, the dialysate circulation. Preferably the filter is designed to be changeable if any of the inlets or outlets are clogged by particles. Suitable materials for the filter inc.ude Millipore cellulose membrane material.

Different components of the system may be connected by way, for example, of silicone tubing, preferably silicone tubing which meets the standards for such tubing when employed in routine dialysis treatment.

Macroporous microcarriers provide both an external surface and an interior space to which hepatocytes grown in suspension can attach. In this way, macroporous microcarriers enhance productivity by increasing cell density per reactor volume. The concentration of hepatocytes on macroporous microcarriers can reach as high as $10^8$/ml.

Macroporous microcarrier culture may start with inoculation of hepatocytes 4 onto microcarriers 5. Hepatocytes 4 are harvested, in a logarithmic growth phase and in a good nutritional state, by protease digestion and transferred to the flasks to allow cellular attachment to the microcarriers 5 with an even distribution. After 5 hours, culture medium is added to the final volume. In order to obtain sufficient cell number, a fluidized bed culture system may be used to scale-up the productivity. The high cell density afforded by macroporous microcarriers 5 results in rapid consumption of any available metabolites. Preferably steady state is maintained at a set level by medium perfusion and oxygen supply systems. Cell growth can be monitored by biochemical determinations and cell counting. Cells 4 may be harvested when the cells become confluent on the macroporous microcarriers 5.

Macroporous microcarriers 5 with well-grown hepatocytes 4 are transferred to containment vessel 43 of bioreactor 3 in a sterile manner by way of top opening 30. The amount of transferred cells may range from 5 to $7.5 \times 10^{10}$, usually $5 \times 10^{10}$. The optimal amount of transferred cells amount in the bioreactor is largely dependent on the clinical requirements of the patients, and thus the severity of the patient's disease state.

After transferring the macroporous microcarriers, bioreactor 3 is initially filled with fresh medium containing 10–30% human serum or plasma William's E medium. The circuit connected with bioreactor 3 is also filled with medium as dialysate flows through the extracapillary space of plasma filtration system 1. The dialysate is circulated by a peristaltic pump 23.

Functional hepatocytes are maintained by a continuous flow of nutrient medium across dialysis membrane 6, and by diffusion of toxic cell waste products across dialysis membrane 6 to medium reservoir 34. A preferred membrane exclusively allows the free passage of small molecules such as amino acids and mercapturic acids between intracapillary and extracapillary spaces. Preferably dialysis membrane 6 is not permeable to high molecular weight compounds, such as plasma proteins. A suitable membrane for the latter purpose has a molecular cut-off ranging from 12,000–14,000 kDalton. A cellulose membrane is preferred. Other membranes that can be used with the present invention include those fabricated from polysulphone, polypropylene, and etc. The composition comprising the dialysate may be William's E without serum. The medium reservoir may be changed over a definite time while the patient circulation is started.

Nutrient medium from medium reservoir 34 may cross the semi-permeable membrane of dialysis cartridge 6 to feed the hepatocytes 4 on microcarriers 5. Cell waste products and toxin conjugates may be removed by dialysis. The dialysate is changed periodically. In this way, the system replaces the excretory function of the liver.

What is claimed is:

1. An improved extracorporeal liver-assist device of the prior art of the type including a human liver-derived cell line, wherein the improvement comprises: a reactor containing a human liver-derived cell line artificially-modified to display at least about twice the GSH content as compared to the same human liver-derived cell line that is not artificially-modified.

2. The improved extracorporeal liver-assist device of claim 1 wherein the human liver-derived cell line is further artificially-modified to display an elevated GST activity as compared to the same human liver-derived cell line that is not artificially-modified.

3. The improved extracorporeal liver-assist device of claim 1 wherein the human liver-derived cell line is an immortal cell line.

4. An improved extracorporeal liver-assist device of the prior art of the type including a human liver-derived cell line, wherein the improvement comprises: a reactor containing a human cell line artificially-modified to display increased GSH content and elevated GST activity.

5. An improved extracorporeal liver-assist device of the prior art of the type including a human liver-derived cell line, wherein the improvement comprises: a reactor containing a human liver-derived cell line having been previously exposed to a compound for a sufficient length of time that the compound causes said cell line to elicit at least about twice the GSH content as compared to the same cell line not previously exposed to said compound.

6. The improved extracorporeal liver-assist device of claim 5 wherein the human liver-derived cell line is an immortalized cell line.

7. The improved extracorporeal liver-assist device of claim 5 wherein the compound to which said human liver-derived cell line has been previously exposed is cisplatin.

8. The improved extracorporeal liver-assist device of claim 5 wherein the human liver-derived cell line is previously exposed to said compound for a period of time of at least one month.

9. The improved extracorporeal liver-assist device of claim 5 wherein the human liver-derived cell line is previously exposed to increasing concentrations of the compound over a period of time of at least one month.

10. An improved extracorporeal liver-assist device of the prior art of the type including a human liver-derived cell line, wherein the improvement comprises: a reactor containing a human cell line having been previously exposed to a compound which elicits increased GSH content and elevated GST activity in such cell line, said cell line being associated with a biocompatible support matrix system.

11. The improved extracorporeal liver-assist device of claim 10 wherein the biocompatible support matrix system comprises macroporous microcarriers.

12. The improved extracorporeal liver-assist device of claim 10 wherein the biocompatible support matrix system comprises a ceramic.

* * * * *